United States Patent [19]

Losee et al.

[11] 4,198,509
[45] Apr. 15, 1980

[54] MERCAPTOACYLPIPERAZINE CARBOXYLIC ACID COMPOUNDS

[75] Inventors: Kathryn A. Losee; Jack Bernstein, both of New Brunswick, N.J.

[73] Assignee: E. R. Squibb & Sons, Inc., Princeton, N.J.

[21] Appl. No.: 955,854

[22] Filed: Oct. 30, 1978

[51] Int. Cl.$^2$ ............... C07D 241/06; A61K 31/495; C07D 241/18
[52] U.S. Cl. ..................... 544/388; 544/357; 424/250
[58] Field of Search ............ 544/387, 357, 388

[56] References Cited
U.S. PATENT DOCUMENTS

| | | | |
|---|---|---|---|
| 3,147,261 | 9/1964 | Modd et al. | 544/387 |
| 4,046,889 | 9/1977 | Ondetti et al. | 424/244 |
| 4,105,776 | 8/1978 | Ondetti et al. | 424/274 |

*Primary Examiner*—Jose Tovar
*Attorney, Agent, or Firm*—Lawrence S. Levinson; Merle J. Smith; Stephen B. Davis

[57] ABSTRACT

The mercaptoacylpiperazine carboxylic acid compounds which have the formula

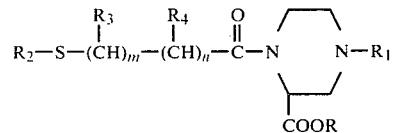

wherein
R, $R_3$ and $R_4$ each is hydrogen or lower alkyl;
$R_1$ is lower alkyl;
$R_2$ is hydrogen, lower alkanoyl, benzoyl or

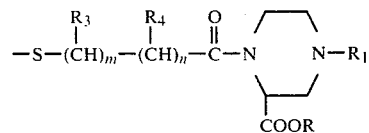

m is 0, 1 or 2;
n is 1, 2 or 3, the sum of m+n being equal to 1, 2 or 3
and salts thereof, are useful as hypotensive agents.

7 Claims, No Drawings

MERCAPTOACYLPIPERAZINE CARBOXYLIC ACID COMPOUNDS

SUMMARY OF THE INVENTION

This invention relates to new mercaptoacylpiperazine carboxylic acid compounds and salts thereof, having utility as hypotensive agents which have the formula $$R_2-S-(CH)_m-(CH)_n-C(=O)-N\underset{COOR}{\diagup\hspace{-0.5em}\diagdown}N-R_1 \quad (I)$$
(with $R_3$ on first CH, $R_4$ on second CH)

wherein
R, $R_3$ and $R_4$ each is
hydrogen or lower alkyl;
$R_1$ is lower alkyl;
$R_2$ is hydrogen, lower alkanoyl, benzoyl or $$-S-(CH)_m-(CH)_n-C(=O)-N\underset{COOR}{\diagup\hspace{-0.5em}\diagdown}N-R_1$$

m is 0, 1 or 2;
n is 1, 2 or 3, the sum of m+n being equal to 1, 2 or 3.

The asterisks indicate asymmetric carbon atoms. The carbons in the mercaptoacyl side chain are asymmetric when $R_3$ and/or $R_4$ is other than hydrogen.

DETAILED DESCRIPTION

The lower alkyl groups represented by the symbols are straight or branched chain hydrocarbon radicals having up to seven carbons like methyl, ethyl, propyl, isopropyl, butyl, isobutyl, t-butyl and the like. The $C_1$–$C_4$ members, especially the $C_1$–$C_2$ members, are preferred.

The lower alkanoyl groups are those having the acyl radicals of the lower (up to seven carbons) fatty acids like acetyl, propionyl, butyryl, isobutyryl and the like. Similarly, those lower alkanoyl groups having up to four carbons, and especially acetyl, are preferred.

A preferred group of compounds are those wherein R and $R_3$ each is hydrogen; $R_1$ is lower alkyl, especially methyl; $R_2$ is hydrogen or lower alkanoyl, especially acetyl; $R_4$ is hydrogen or lower alkyl, especially methyl; m is 0 or 1; and n is 1.

The products of this invention have one or more asymmetric carbon atoms as indicated by the asterisks in formula I. The compounds accordingly exist in stereoisomeric forms or in racemic mixtures thereof. All of these are within the scope of the invention. In general, the L-isomer with respect to the carbon of the piperazine carboxylic acid constitutes the preferred isomeric form.

The compounds of formula I are produced by reacting a 4-lower alkylpiperazine-2-carboxylic acid having the formula $$HN\underset{COOH}{\diagup\hspace{-0.5em}\diagdown}N\text{-lower alkyl} \quad (II)$$

preferably in the form of an acid salt, e.g., the salt of a mineral acid like hydrochloric acid, hydrobromic acid or the like, with an acylthioacyl halide having the formula $$R_5-S-(CH)_m-(CH)_n-C(=O)-hal \quad (III)$$
(with $R_3$, $R_4$ substituents)

wherein
$R_3$ and $R_4$ have the meaning defined above,
$R_5$ is lower alkanoyl or benzoyl, and
hal is a halogen, preferably chlorine or bromine.

This reaction is carried out in an inert organic solvent, e.g., dimethylformamide, dimethylacetamide or the like, in the presence of an acid acceptor like N-methylmorpholine, triethylamine etc. Heat, e.g., in the range of about 30° to 80° C., accelerates the reaction. A compound of formula I wherein $R_2$ is lower alkanoyl or benzoyl is thus obtained.

The acyl group $R_5$ can be removed and the compound of formula I wherein $R_2$ is hydrogen can be obtained by treating the product of the above reaction with a base like ammonium hydroxide or sodium hydroxide.

The disulfides, i.e., compounds of formula I wherein $R_2$ is the radical $$-S-(CH)_m-(CH)_n-C(=O)-N\underset{COOR}{\diagup\hspace{-0.5em}\diagdown}N-R_1$$

are produced by directly oxidizing with iodine a compound of formula I in which $R_2$ is hydrogen.

The compounds of formula I, wherein R is a lower alkyl group and $R_2$ is lower alkanoyl, benzoyl or $$-S-(CH)_m-(CH)_n-C(=O)-N\underset{COOR}{\diagup\hspace{-0.5em}\diagdown}N-R_1$$

are produced by reacting a compound of formula I wherein R is hydrogen and $R_2$ is hydrogen, lower alkanoyl, benzoyl or $$-S-(CH)_m-(CH)_n-C(=O)-N\underset{COOR}{\diagup\hspace{-0.5em}\diagdown}N-R_1$$

with a diazoalkane such as diazomethane, diazoethane, diazopropane or the like in an inert solvent such as methanol, ethanol, diethyl ether or the like. Alternatively, an alkyl 3-p-tolyltriazene may be used instead of the diazoalkane.

In those cases in which $R_2$ is other than hydrogen, the desired ester may be obtained by treatment with a lower alkanol such as methanol or ethanol and a dehydrating agent such as dicyclohexylcarbodiimide or 1,1'-carbonyldiimidazole.

When a compound of formula I is thus obtained, in which $R_2$ is a lower alkanoyl or benzoyl group, the compound may be converted to a compound of formula I in which $R_2$ is hydrogen by removing the acyl group with dilute aqueous ammonia or sodium hydroxide.

Alternatively the compounds of formula I, wherein R is a lower alkyl group and $R_2$ is as defined previously, may be obtained by acylating a compound of the formula

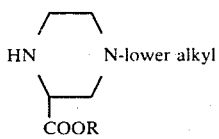

with an acylthioacyl halide of formula III in an inert solvent, e.g., dimethylformamide, dimethylacetamide or the like in the presence of an acid acceptor, like N-methylmorpholine, triethylamine, etc.

The compounds of this invention form acid or basic salts depending upon pH. The compounds of this invention wherein R is hydrogen form basic salts with various inorganic or organic bases. Such salts include alkali metal salts, especially sodium and potassium, alkaline earth metal salts, especially calcium and magnesium, aluminum, dicyclohexylamine salt, benzathine salt, N-methylglucamine salt, hydrabamine salt, salts with naturally occurring amino acids like arginine, lysine and the like, lower alkylamine salts like the methylamine, ethylamine, dimethylamine, triethylamine salts, etc.

These compounds of this invention also form conventional acid addition salts with various inorganic and organic acids such as hydrochloric acid, hydrobromic acid, phosphoric acid and the like, as well as acetic acid, tartaric acid and other pharmaceutically acceptable acids. They are also included in the scope of the invention. The nontoxic, physiologically acceptable salts are preferred, although other salts are also useful, e.g., in isolating or purifying the product. The salts are formed in conventional manner by reacting the free acid form of the product with one or more equivalents of the appropriate base providing the desired salt ion in a solvent or medium in which the salt is insoluble, or in water and removing the water by freeze drying or by reacting with an acid such as those named above. By neutralizing the salt by conventional methods, the free acid form can be obtained, and if desired, another salt formed.

The 4-alkylpiperazine-2-carboxylic acids of formula II which are starting materials are produced from N-benzylethanolamine and thionyl chloride by the method described in J. Chem. Soc., 1955, p 898. The N-benzyl-2-chlorethylamine hydrochloride which is the product of this reaction is used to react with an excess of primary alkylamine ($R_1$–$NH_2$) to obtain the desired N-benzyl-N'-lower alkylethylenediamine. Condensation of this diamine with a lower alkyl 2,3-dibromopropionate yields the 4-lower alkylpiperazine-2-carboxylic acid lower alkyl ester. [See Helv. Chim. Acta 45, 2383 (1962) for the foregoing methodology]. Hydrolysis of the ester with concentrated mineral acid, e.g., hydrochloric acid, gives 4-lower alkylpiperazine-2-carboxylic acid.

The acyl halides of formula III are produced by the known methods of halogenating the corresponding carboxylic acid, e.g., with thionyl chloride.

Additional experimental details are found in the examples which are preferred embodiments and also serve as models for the preparation of other members of the group.

The compounds of this invention inhibit the conversion of the decapeptide angiotensin I to angiotensin II by angiotensin converting enzyme and therefore are useful in reducing or relieving angiotensin related hypertension, for example, renovascular hypertension or malignant hypertension. By the administration of a composition containing one or a combination of compounds of formula I or physiologically acceptable salt thereof, angiotensin dependent hypertension in the species of mammal, e.g., rats, cats, dogs, etc., suffering therefrom is reduced or alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitonealy can also be employed.

The compounds of this invention can be utilized to achieve the reduction of blood pressure by formulating in conventional compositions such as tablets, capsules or elixirs for oral administration or in sterile solutions or suspensions for parenteral administration. About 10 to 500 mg. of a compound or mixture of compounds of formula I or physiologically acceptable salts is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention and constitute especially preferred embodiments. All temperatures are in degrees Celsius.

EXAMPLE 1

(a) N-Benzyl-2-chlorethylamine 100 ml. of thionyl chloride are added to a stirred solution of 100 g. of 2-benzylaminoethanol in 500 ml. of chloroform over a period of 20 minutes. The mixture is refluxed for 6 hours. 1350 ml. of ether is added to the cooled chloroform solution and the mixture is stored in the refrigerator overnight. The product, N-benzyl-2-chlorethylamine hydrochloride, is filtered off and crystallized from ethanol-ether; yield 130.9 g., m.p. 192°–194°.

(b) N-Benzyl-N'-methylethylenediamine 130.6 g. of N-benzyl-2-chlorethylamine hydrochloride and 800 ml. of 7.4 N monomethylamine in absolute alcohol are heated at 50° for 16 hours then concentrated to dryness. The residue is dissolved in 400 ml. of benzene. To this is added a solution of 120 g. of potassium hydroxide in 185 ml. of water. The benzene is separated and dried (MgSO$_4$) and evaporated to yield 88.4 g. of liquid residue which is fractionated to yield 63 g. (61%) of N-benzyl-N'-methylethylenediamine, b.p. 0.2 mm 80°–84°.

(c) 1-Benzyl-4-methylpiperazine-2-carboxylic acid, ethyl ester

To 63 g. of N-benzyl-N'-methylethylenediamine in 400 ml. of benzene are added 88.8 g. of ethyl 2,3-dibromopropionate and 124 g. of triethylamine. The mixture is stirred at 80° for 3 hours. The solid material is filtered off. The filtrate is diluted with 200 ml. of benzene and washed free of bromide ion with water, then dried (MgSO$_4$). The solvent is removed and the residue is distilled to yield 73.2 g. (73%) of 1-benzyl-4-methylpiperazine-2-carboxylic acid ethyl ester, b.p. 0.4 mm 125°–128°.

(d) 4-methylpiperazine-2-carboxylic acid, ethyl ester 13.1 g. of 1-benzyl-4-methylpiperazine-2-carboxylic acid, ethyl ester in 100 ml. of absolute alcohol and 3 g. of palladium on charcoal are shaken at room temperature and 50 psi for 4½ hours. The catalyst is filtered off and the residue is distilled to obtain 4-methylpiperazine-2-carboxylic acid, ethyl ester, b.p. 0.3 mm 84°–86°.

(e) 4-Methylpiperazine-2-carboxylic acid dihydrochloride 30 g. of 4-methylpiperazine-2-carboxylic acid, ethyl ester in 255 ml. of concentrated hydrochloric acid are refluxed for 4 hours. The solvent is then removed and the tacky residue is triturated with cold methanol to yield 34.6 g. (93%) of solid 4-methylpiperazine-2-carboxylic acid, dihydrochloride, m.p. 172°–174°.

Additional 4-lower alkylpiperazine-2-carboxylic acids and esters are produced in the same manner by substituting the appropriate alkylamine for the methylamine in part b.

EXAMPLE 2

1-[3-(Acetylthio)-1-oxopropyl]-4-methylpiperazine-2-carboxylic acid 4.34 g. of 4-methylpiperazine-2-carboxylic acid, dihydrochloride are suspended in 100 ml. dimethylformamide and at 20° 6.06 g. of N-methylmorpholine is added. 3.32 g. of 3-acethylthiopropanoyl chloride are added. The mixture is heated with stirring at 75°–80° for about 5 hours. A clear solution forms after ½ hour heating. After cooling, the solid N-methylmorpholine hydrochloride is removed by filtration. The solvent is removed under reduced pressure to yield 15.8 g. of residue. 6 g. of this residue is dissolved in 100 ml. of ethanol and passed through a column of AG50W-X2 ion exchange resin (pre-washed). The column is washed with water until free of acid and then eluted with pyridyl acetate buffer (pH 6.5) until the pH becomes constant at 6.5. About 300 ml. of buffer are used. The buffer extracts are lyophilized to yield a brown-yellow solid which is dissolved in 100 ml. of water, decolorized with charcoal and lyophilized again to yield 1 g. (36%) of solid 1-[3-(acetylthio)-1-oxopropyl]-4-methylpiperazine-2-carboxylic acid, m.p. 92°–98° (softening at 92°).

EXAMPLE 3

DL-1-(3-Mercapto-1-oxopropyl)-4-methylpiperazine-2-carboxylic acid 6 ml. of concentrated ammonium hydroxide is stirred at 10°, under nitrogen for about 15 minutes. Then 3.6 g. (0.013 m.) of 1-[3-(acetylthio)-1-oxopropyl]-4-methylpiperazine-2-carboxylic acid is added and a clear solution forms. The ice bath is removed and the solution is stirred under nitrogen at room temperature for 2 hours. It is then passed through a column of pre-washed ion exchange resin AG50W-X2. The product is eluted with pH 6.5 pyridine acetate buffer until no more SH positive material is detected (about 350 ml. of buffer solution is used). The total volume is adjusted to 40 ml. (pH 6.5) and the solution is lyophilized to yield 3.4 g. of solid which smells faintly of pyridine. It is redissolved in 100 ml. of water (pH 5.5) and lyophilized again to yield 2.3 g. (76%) of product DL-1-(3-mercapto-1-oxopropyl)-4-methylpiperazine-2-carboxylic acid, m.p. 75°–79°.

EXAMPLE 4

DL-1-(3-Mercapto-1-oxopropyl)-4-methylpiperazine-2-carboxylic acid, n-propyl ester To a stirred suspension of 11.6 gms. of DL-1-(3-mercapto-1-oxopropyl)-4-methylpiperazine-2-carboxylic acid in 150 ml. of ether there is added dropwise a solution of diazopropane in ether [prepared from 8.75 g. of N'-nitro-N-nitroso-N-propylguanidine by the procedure of McKay et al. Can. J. Res. 28 B, 683(1950)]. The mixture is stirred for an additional three hours, filtered and washed twice with 100 ml. of 5% aqueous sodium bicarbonate solution. The ether solution is dried over anhydrous magnesium sulfate, and then concentrated under atmospheric pressure, leaving as a residue the desired DL-1-(3-mercapto-1-oxopropyl)-4-methylpiperazine-2-carboxylic acid, n-propyl ester.

The hydrochloride salt is obtained by dissolving the above product in an equivalent amount of N hydrochloric acid and lyophilizing.

EXAMPLE 5

DL-1-(3-Acetylthio-1-oxopropyl)-4-methylpiperazine-2-carboxylic acid, n-propyl ester Following the procedure of Example 4, but substituting DL-1-(3-acetylthio-1-oxopropyl)-4-methylpiperazine-2-carboxylic acid for an equivalent amount of DL-1-(3-mercapto-1-oxopropyl)-4-methylpiperazine-2-carboxylic acid, there is obtained the desired DL-1-(3-acethylthio-1-oxopropyl)-4-methylpiperazine-2-carboxylic acid, n-propyl ester.

EXAMPLE 6

1,1'-[Dithiobis(1-oxopropane)-3,1-diyl]bis(4-methylpiperazine-2-carboxylic acid)

A solution of 6.96 gms. of 1-(3-mercapto-1-oxopropyl)-4-methylpiperazine-2-carboxylic acid in 150 ml. of water is adjusted to pH 6.5 by the addition of an aqueous solution of normal aqueous sodium hydroxide. To this solution there is added dropwise, with vigorous stirring an 0.5 molar alcoholic iodine solution (approximately 30 ml.) until the iodine color persists. The pH is maintained between 5.5 and 7.0 by the addition of normal sodium hydroxide solution. The excess iodine is removed by the addition of dilute aqueous sodium thiosulfate.

The reaction mixture is then concentrated under reduced pressure to remove the alcohol and the residue dissolved in a small amount of water and neutralized by the addition of hydrochloric acid. The precipitate is purified by crystallization from methanol, yielding the desired 1,1′-[dithiobis(1-oxopropane)-3,1-diyl]bis(4-methylpiperazine-2-carboxylic acid).

EXAMPLE 7

1,1′-[Dithiobis(1-oxopropane-3,1-diyl)]bis(4-methylpiperazine-2-carboxylic acid, n-propyl ester)

Following the procedure of Example 4 but substituting an equivalent amount of 1,1′-[dithiobis(1-oxopropane-3,1-)]bis(4-methylpiperazine-2-carboxylic acid) for the DL-1-(3-mercapto-1-oxopropyl)-4-methylpiperazine-2-carboxylic acid there is obtained the desired 1,1′-[dithiobis-(1-oxopropane-3,1-diyl)]bis(4-methylpiperazine-2-carboxylic acid, n-propyl ester).

EXAMPLE 8

DL-1-(3-Acetylthio-2-methyl-1-oxopropyl)-4-ethylpiperazine-2-carboxylic acid

Following the procedure of Example 1e but substituting an equivalent amount of 4-ethylpiperazine-2-carboxylic acid, ethyl ester for the 4-methylpiperazine-2-carboxylic acid, ethyl ester there is obtained the desired 4-ethylpiperazine-2-carboxylic acid, dihydrochloride.

Following the procedure of Example 2, but substituting an equivalent amount of 4-ethylpiperazine-2-carboxylic acid dihydrochloride for the 4-methylpiperazine-2-carboxylic acid dihydrochloride and an equivalent amount of 3-acethylthio-2-methylpropanoyl chloride for the 3-acetylthiopropanoyl chloride, there is obtained the desired DL-1-(3-acethylthio-2-methyl-1-oxopropyl)-4-ethylpiperazine-2-carboxylic acid.

EXAMPLE 9

DL-1-(3-Acetylthio-1-oxopropyl)-4-methylpiperazine-2-carboxylic acid, n-butyl ester To a vigorously stirred solution of 8.22 gms. of DL-1-(3-acetylthio-1-oxopropyl)-4-methylpiperazine-2-carboxylic acid in 100 ml. of dry ethylene glycol dimethyl ether there is added 4.86 gms. of 1,1′-carbonyldiimidazole and the stirring continued for 2 hours. To this solution there is added 2.22 gms. of n-butanol in 50 ml. of dry ethylene glycol dimethyl ether followed by 100 mg. of sodamide.

The reaction mixture is stirred for 24 hours and then concentrated under reduced pressure. The residue is dissolved in 250 ml. of dichloromethane and washed with three 75 ml. portions of saturated sodium chloride solution and twice with 100 ml. portions of saturated sodium bicarbonate solution. The solution is dried over anhydrous magnesium sulfate and is then concentrated to yield the desired DL-1-(3-acetylthio-1-oxopropyl)-4-methylpiperazine-2-carboxylic acid, n-butyl ester.

EXAMPLE 10

1-[2-(Benzoylthio)-1-oxoethyl]-4-methylpiperazine-2-carboxylic acid

To a suspension of 4.34 gms. of 4-methylpiperazine-2-carboxylic acid dihydrodichloride in 100 ml. of dimethylformamide is added 6.06 gms. of N-methylmorpholine, followed by the dropwise addition of a solution of 4.3 gms. of 2-benzoylthioacetyl chloride in 50 ml. of dimethylformamide. The reaction mixture is stirred for one hour at room temperature and for 5 hours at 70°–80°. The reaction mixture is then cooled, filtered and concentrated under reduced pressure. The residue is dissolved in ethanol and poured through a column of AG50W-42 ion exchange resin. The column is washed with water until the washings are acid-free and the product eluted with pyridylacetate buffer (pH 6.5). The buffer eluates are lyophilized to yield the crude product. This is dissolved in water, treated with decolorizing carbon and lyophilized to yield the product 1-[2-(benzoylthio)-1-oxoethyl]-4-methylpiperazine-2-carboxylic acid.

EXAMPLE 11

1-[4-(Acetylthio)-1-oxobutyl]-4-methylpiperazine-2-carboxylic acid

Following the procedure of Example 10 but substituting an equivalent amount of 4-acethylthiobutyroyl chloride for the 2-benzoylthioacetyl chloride, there is obtained 1-[4-(acetylthio)-1-oxobutyl]-4-methylpiperazine-2-carboxylic acid.

The sodium salt is obtained by dissolving the above product in an equimolar amount of cold N/10 sodium bicarbonate and lyophilizing.

EXAMPLE 12

1-(4-Mercapto-1-oxobutyl)-4-methylpiperazine-2-carboxylic acid

Following the procedure of Example 3 but substituting an equivalent amount of 1-[4-(acetylthio)-1-oxobutyl]-4-methylpiperazine-2-carboxylic acid for the 1-[3-(acethylthio)-1-oxopropyl]-4-methylpiperazine-2-carboxylic acid there is obtained 1-(4-mercapto-1-oxobutyl)-4-methylpiperazine-2-carboxylic acid.

What is claimed is:

1. A compound of the formula $$R_2-S-(CH)_m-(CH)_n-\overset{O}{\overset{\|}{C}}-N\underset{\underset{COOR}{|}}{\overset{R_3\quad R_4}{\diagup\diagdown}}N-R_1$$

wherein

R, $R_3$ and $R_4$ each is hydrogen or lower alkyl;
$R_1$ is lower alkyl;
$R_2$ is hydrogen, lower alkanoyl, benzoyl or $$-S-(CH)_m-(CH)_n-\overset{O}{\overset{\|}{C}}-N\underset{COOR}{\diagup\diagdown}N-R_1$$

m is 0, 1 or 2;
n is 1, 2 or 3, the sum of m+n being equal to 1, 2 or 3;
and salts thereof.

2. A compound as in claim 1 wherein R and $R_2$ each is hydrogen.

3. A compound as in claim 1 wherein $R_2$ is lower alkanoyl.

4. A compound as in claim 1 wherein $R_1$ is methyl.

5. A compound as in claim 1 wherein R and $R_3$ each is hydrogen; $R_1$ is lower alkyl; $R_2$ is hydrogen or lower alkanoyl; $R_4$ is hydrogen or lower alkyl; m is 0 or 1; and n is 1.

6. A compound as in claim 1 wherein R, $R_3$ and $R_4$ each is hydrogen; $R_1$ is methyl; $R_2$ is acetyl; and m and n each is 1.

7. A compound as in claim 1 wherein R, $R_2$, $R_3$ and $R_4$ each is hydrogen; $R_1$ is methyl; and m and n each is 1.

* * * * *